United States Patent
Kwong et al.

(10) Patent No.: US 10,273,520 B2
(45) Date of Patent: *Apr. 30, 2019

(54) **MEANS AND METHODS FOR HYPER-PRODUCTION OF AUTHENTIC HUMAN BASIC FIBROBLAST GROWTH FACTOR IN *ESCHERICHIA COLI***

(71) Applicant: Wan Keung Raymond Wong, Hong Kong (HK)

(72) Inventors: Wai Yeung Kwong, Hong Kong (HK); Wan Keung Raymond Wong, Hong Kong (HK)

(73) Assignee: Wan Keung Raymond Wong, Hong Kong (HK)

(*) Notice: Subject to any disclaimer, the term of this patent is extended or adjusted under 35 U.S.C. 154(b) by 0 days.

This patent is subject to a terminal disclaimer.

(21) Appl. No.: 15/409,137

(22) Filed: Jan. 18, 2017

(65) Prior Publication Data
US 2017/0183704 A1   Jun. 29, 2017

Related U.S. Application Data

(63) Continuation-in-part of application No. 14/781,614, filed as application No. PCT/CN2014/072531 on Feb. 25, 2014, now Pat. No. 9,580,484.

(60) Provisional application No. 61/808,602, filed on Apr. 4, 2013.

(30) Foreign Application Priority Data

Aug. 31, 2016 (HK) .................... 16110349

(51) Int. Cl.
| | | |
|---|---|---|
| *C12P 21/02* | (2006.01) | |
| *C12N 15/72* | (2006.01) | |
| *C12N 9/14* | (2006.01) | |
| *C12N 15/70* | (2006.01) | |

(52) U.S. Cl.
CPC ............... *C12P 21/02* (2013.01); *C12N 9/14* (2013.01); *C12N 15/70* (2013.01); *C12N 15/72* (2013.01); *C12Y 306/00* (2013.01)

(58) Field of Classification Search
None
See application file for complete search history.

(56) References Cited

U.S. PATENT DOCUMENTS

| | | | |
|---|---|---|---|
| 5,646,015 A | 7/1997 | Wong et al. | |
| 7,517,528 B2 | 4/2009 | Wong et al. | |
| 9,580,484 B2* | 2/2017 | Wong | C07K 14/503 |
| 2001/0051148 A1 | 12/2001 | Tremblay | |
| 2007/0065912 A1* | 3/2007 | Carson | C07K 16/00 435/69.1 |
| 2007/0092489 A1 | 4/2007 | Fishbein et al. | |
| 2008/0254512 A1 | 10/2008 | Capon | |

OTHER PUBLICATIONS

Alibolandi, et al., Purification and Refolding of Overexpressed Human Basic Fibroblast Growth Factor in *Escherichia coli*,, SAGE-Hindawi Access to Research, Biotechnology Research International, vol. 2011, Article ID 973741, Jun. 8, 2011.

Andrades, et al., Production of a Recombinant Human Basic Fibroblast Growth Factor with a Collagen Binding Domain, Protoplasma, 218: 95-103, Springer-Verlag, Austria, 2001.

Barr, et al., Expression and Processing of Biologically Active Fibroblast Growth Factors in the Yeast *Saccharomyces cerevisiae*\*, The Journal of Biological Chemistry, vol. 263, No. 31, Issue of Nov. 5, pp. 16471-16478, 1988, U.S.A.

Bikfalvi, et al., Biological Roles of Fibroblast Growth Factor-2\*, Endocrine Reviews, vol. 18, No. 1, 1997, U.S.A.

Chan, et al., Cloning and Characterization of a Novel Cellobiase Gene, cba3, Encoding the First Known β-Glucosidase of Glycoside Hydrolase Family 1 of *Cellulomonas biazotea*, Gene, vol. 493 (2012), pp. 52-61, Elsevier (2012).

Cottingham, et al., A Method for the Amidation of Recombinant Peptides Expressed as Intein Fusion Proteins in *Escherichia coli*, Nature Biotechnology, vol. 19, pp. 974-977, Oct. 2001, Nature Publishing Group.

Elleuche, et al., Inteins, Valuable Genetic Elements in Molecular Biology and Biotechnology, Appl Microbiol Biotechnical, 87, pp. 479-489, 2010, Springer.

Esipov, et al., Production of Recombinant Human Epidermal Growth Factor using Ssp dnaB Mini-Intein System, Protein Expression and Purification, vol. 61, pp. 1-6, 2008, Elsevier.

Ferrer-Miralles, et al., Microbial Factories for Recombinant Pharmaceuticals, Microbial Cell Factories, vol. 8, pp. 17-25, 2009.

Fu, et al., Cell Death Caused by Hyper-Expression of a Secretory Exoglucanase in *Escherichia coli*, Protein Expression & Purification, vol. 42, pp. 67-77, 2005, Elsevier.

Fu, et al., A Two-Stage Refinement Approach for the Enhancement of Excretory Production of an Exoglucanase from *Escherichia coli*, Protein Expression & Purification, vol. 48, pp. 205-214, 2006, Elsevier.

Garke, et al., Preparative Two-Step Purification of Recombinant Human Basic Fibroblast Growth Factor from High-Cell-Density Cultivation of *Eschericia coli*, Journal of Chromatography B, vol. 737, pp. 25-38, 2000, Elsevier.

Huang, et al., Human Epidermal Growth Factor Excreted by Recombinant *Escherichia coli* K-12 has the Correct N-terminus and is Fully Bioactive, Process Biochemistry, vol. 35, pp. 1-5, 1999, Elsevier.

(Continued)

*Primary Examiner* — James S Ketter
(74) *Attorney, Agent, or Firm* — Heslin Rothenberg Farley and Mesiti, PC; Kathy Smith Dias; Melvin Li

(57) ABSTRACT

The present invention is concerned with a method of production of authentic human epidermal growth factor (EGF) and hyper-production of authentic basic fibroblast growth factor (bFGF) without any modification at either C- or N-terminal of the bFGF.

4 Claims, 7 Drawing Sheets

(56) References Cited

OTHER PUBLICATIONS

Ingham, et al., A Versatile System for the Expression of Nonmodified Bacteriocins in *Escherichia coli*, Journal of Applied Microbiology, vol. 98, pp. 676-686, 2005.

Kwong, et al., Authentic Human Basic Fibroblast Growth Factor Produced by Secretion in *Bacillus subtilis*, Appl Microbiol Biotechnical, vol. 97, pp. 6803-6811, 2013, Springer.

Lam, et al., Enhancement of Extracellular Production of a *Cellulomonas fimi* Exoglucanase in *Escherichia coli* by the Reduction of Promoter Strength, Enzyme and Microbial Technology, vol. 20, pp. 482-488, 1997, Elsevier.

Lee, et al., Genetic Studies on the Inability of β-Galactosidase to be Translocated Across the *Escherichia coli* Cytoplasmic Membrane, Journal of Bacteriology, vol. 171, No. 9, pp. 4609-4616, Sep. 1989.

Li, Yifeng, Self-Cleaving Fusion Tags for Recombinant Protein Production, Biotechnology Letters, vol. 33, pp. 869-881, 2011, Springer.

Mirzahoseini, et al., Differential Expression of Human Basic Fibroblast Growth Factor in *Escherichia coli*: Potential Role of Promoter, World Journal of Microbiology & Biotechnology, vol. 20, pp. 161-165, 2004, Khwer Academic Publishers, Netherlands.

Mu, et al., High-Level Expression, Purification, and Characterization of Recombinant Human Basic Fibroblast Growth Factor in *Pichia pastoris*, Protein Expression & Purification, vol. 59, pp. 282-288, 2008, Elsevier.

Nakayama, et al., Efficient Secretion of the Authentic Mature Human Growth Hormone by *Bacillus subtilis*, pp. 123-134, 1988, Elsevier.

Sellke, et al., Therapeutic Angiogenesis with Basic Fibroblast Growth Factor: Technique and Early Results, The Annals of Thoracic Surgery, vol. 65, pp. 1540-1544, 1998.

Sheng, et al., Expression and Purification of a Biologically Active Basic Fibroblast Growth Factor Fusion Protein, Protein Expression and Purification, vol. 27, pp. 267-271, 2003, Elsevier Science (USA).

Sivakesava, et al., Production of Excreted Human Epidermal Growth Factor (hEGF) by an Efficient Recombinant *Escherichia coli* System, Process Biochemistry, vol. 34, pp. 893-900, 1999, Elsevier.

Wang, et al., Expression of Intein-Tagged Fusion Protein and Its Applications in Downstream Processing, Journal of Chemical Technology and Biotechnology, vol. 85, pp. 11-18, 2010.

Wang, et al., Enhancement of Excretory Production of an Exoglucanase from *Escherichia coli* with Phage Shock Protein a (PspA) Overexpression, Journal of Microbiology and Biotechnology, 21(6), pp. 637-645, 2011.

Wong, et al., Application of Recombinant Microbial Systems to the Production of Commercially Valuable Proteins, Research Journal of Biotechnology, vol. 3(3), Aug. 2008.

Wong, et al., Applications, and Efficient Large-Scale Production, of Recombinant Human Epidermal Growth Factor, Biotechnology & Genetic Engineering Reviews, vol. 18, Jul. 2001.

Wong, et al., Cloning, Expression, and Characterization of Diuretic Hormone *Manduca* diuresin from *Manduca sexta* in *Escherichia coli*, Protein Expression and Purification, vol. 29, pp. 51-57, 2003, Elsevier.

Wong, et al., Engineering of Efficient *Escherichia coli* Excretion Systems for the Production of Heterologous Proteins for Commercial Applications, Recent Patents on Chemical Engineering, vol. 5, pp. 45-55, 2012, Bentham Science Publishers.

Goeddel, et al., Expression in *Escherichia coli* of Chemically Synthesized Genes for Human Insulin, Proceedings of the National Academy of Sciences, USA, vol. 76, No. 1, pp. 106-110, Jan. 1979.

Wong, et al., Extracellular Expression of Human Epidermal Growth Factor Encoded by an *Escherichia coli* K-12 Plasmid Stabilized by the ytl2-incR System of *Salmonella typhimurium*, Journal of Industrial Microbiology & Biotechnology, vol. 21, pp. 31-36, 1998.

* cited by examiner

MEANS AND METHODS FOR HYPER-PRODUCTION OF AUTHENTIC HUMAN BASIC FIBROBLAST GROWTH FACTOR IN ESCHERICHIA COLI

CROSS REFERENCE TO RELATED APPLICATIONS

The present application claims Paris Convention priority from Hong Kong Patent Application No. 16110349.9 filed Aug. 31, 2016, and is a continuation-in-part application of U.S. patent application Ser. No. 14/781,614 filed Oct. 1, 2015 which claims priority from U.S. Patent Serial Application No. 61/808,062 filed Apr. 3, 2013, contents of all of which are incorporated herein in their entirety.

FIELD OF THE INVENTION

The present invention is concerned with means and method for hyper-production of authentic human basic fibroblast growth factor in *Escherichia coli*.

BACKGROUND OF THE INVENTION

Human basic fibroblast growth factor is a functionally versatile but very expensive polypeptide. While there had been proposals in the past in the production of the polypeptide, many of such proposals were not concerned with producing authentic basic fibroblast growth factor, or the basic fibroblast growth factor produced did not have the native characteristics. For example, the produced basic fibroblast growth factor was not soluble, not bioactive, not cleavable, truncated, and/or with undesired modification to the C- or N-terminal. Further, the level of production was often so low that it could not justify a realistic production in a commercial sense. Yet further, some of the proposals made use of biological system which would generate undesired side products, e.g. toxics, rending the isolation of the human basic fibroblast growth factor not suitable for human application.

Cost-effective production of recombinant authentic proteins is a prerequisite for the widespread availability of the products on the market. Human basic fibroblast growth factor, notwithstanding a versatile protein shown to play important functions in various physiological processes including angiogenesis, wound healing and chondrogenesis, has not been commonly applied as expected. Authentic human basic fibroblast growth factor (bFGF) is a 16.5 kDa protein comprising 146 aa residues. However, essentially only structural analogs of bFGF of various molecular sizes are available for commercial applications. The reason is probably due to the use of conventional cloning methods, which are unable to establish a cost-effective processing protocol, to result in the production of authentic, soluble, bioactive, cleavable or cleaved, non-truncated, free of C- or N-terminal modification to the bFGF. Thus, bFGF has not been commonly available for skin care or therapeutic applications in a wide scale. Incredibly, however, despite being unauthentic, at the time when this description is being prepared bFGF analogs are already sold at extremely high prices, ranging from US$1,300 to US$2,000 per mg. Thus, only an effective method of producing genuine bFGF (and not analogs or bio-similars) cost effectively may allow user to benefit.

The present invention seeks to address the aforementioned issues, or at least to provide an alternative to the public.

SUMMARY OF THE INVENTION

According to a first aspect of the present invention, there is provided a method of production of authentic human epidermal growth factor (EGF) and hyper-production of authentic basic fibroblast growth factor (bFGF) without any modification at either C- or N-terminal of the bFGF, comprising:
providing an *Escherichia coli* host;
introducing a DNA construct into the *Escherichia coli* host to produce a transformed *Escherichia coli* host, the DNA construct including an insert consisting of, in the order of, an expression cassette, a DNA coding sequence for the EGF polypeptide, a first intein sequence, a first copy of a DNA coding sequence for authentic bFGF, a second intein sequence, and a second copy of a DNA coding sequence for the authentic bFGF, but being devoid of an ompA leader sequence;
subjecting the transformed *Escherichia coli* host to a fed-batch fermentation process;
wherein:
the DNA construct is configured to enable the transformed *Escherichia coli* host to produce the authentic bFGF in a soluble form cleaved and independent from proteins encoded by DNA regions preceding and subsequent to the authentic bFGF DNA coding sequences in the insert, and intracellularly;
the fed-batch fermentation process is free of an induction step making use Isopropyl $\beta$-D-1-thiogalactopyranoside (IPTG);
the fed-batch fermentation process includes, during an early log-growth phase, a feeding step for a duration of time of substantially, but less than, 6 hours;
the fed-batch fermentation process includes, after the feeding step, a cultivation step for a duration of time of substantially, but less than, 7 hours; and
the *Escherichia coli* host is configured to produce the bFGF at a concentration at least two times more than a *Escherichia coli* host transformed with the DNA construct but without the second intein sequence and the second copy of a DNA coding sequence for the authentic bFGF can.

Preferably, the concentration of the produced bFGF at the end of the cultivation step may be substantially 610 mg per liter of cell culture.

Suitably, the intein sequences are *Saccharomyces cerevisiae* vascular membrane ATPase (VMA).

According to a second aspect of the present invention, there is provided a method of production of authentic human epidermal growth factor (EGF) and hyper-production of authentic basic fibroblast growth factor (bFGF) without any modification on either C- or N-terminal of the bFGF, comprising:
providing an *Escherichia coli* host;
introducing a DNA construct into the *Escherichia coli* host to produce a transformed *Escherichia coli* host, the DNA construct including an insert comprising, in the order of, an expression cassette, a DNAcoding sequence for the EGF polypeptide, a first intein sequence, a first copy of a DNA coding sequence for authentic bFGF, a second intein sequence, and a second copy of a DNA coding sequence for the authentic bFGF, but being devoid of an ompA leader sequence;
subjecting the transformed *Escherichia coli* host to a fed-batch fermentation process;

wherein:
the DNA construct is configured to enable the transformed *Escherichia coli* host to produce the authentic bFGF in a soluble form cleaved and independent from proteins encoded by DNA regions preceding and subsequent to the authentic bFGF DNA coding sequences in the insert, and intracellularly;
the fed-batch fermentation process is free of an induction step making use Isopropyl β-D-1-thiogalactopyranoside (IPTG);
the fed-batch fermentation process includes, during an early log-growth phase, a feeding step for a duration of time of substantially, but less than, 6 hours;
the fed-batch fermentation process includes, after the feeding step, a cultivation step for a duration of time of substantially, but less than, 7 hours; and
the *Escherichia coli* host is configured to produce the bFGF at a concentration at least two times more than a *Escherichia coli* host transformed with the DNA construct but without the second intein sequence and the second copy of a DNA coding sequence for the authentic bFGF can.

Preferably, the intein sequences may be *Saccharomyces cerevisiae* vascular membrane ATPase (VMA).

Suitably, the concentration of the produced bFGF at the end of the cultivation step may be substantially 610 mg per liter of cell culture.

According to a fourth aspect of the present invention, there is provided a biological system engineered from an *Escherichia coli* host, comprising a DNA construct including an insert consisting of, in the order of, an expression cassette, a DNA coding sequence for the EGF polypeptide, a first intein sequence, a first copy of a DNA coding sequence for authentic bFGF, a second intein sequence, and a second copy of a DNA coding sequence for the authentic bFGF, but being devoid of an ompA leader sequence;
wherein:
the DNA construct is configured to enable the transformed *Escherichia coli* host to produce the authentic bFGF in a soluble form cleaved and independent from proteins encoded by DNA regions preceding and subsequent to the authentic bFGF DNA coding sequence in the insert, and intracellularly;
the system is configured to multiply in a fed-batch fermentation process; and
the *Escherichia coli* host is configured to produce the bFGF at a concentration at least the times more than a *Escherichia coli* host transformed with the DNA construct but without the second intein sequence and the second copy of a DNA coding sequence for the authentic bFGF.

According to a first aspect of the present invention, there is provided a DNA construct for use in a *Escherichia coli* host for production of at least a first polypeptide of an authentic human epidermal growth factor (EGF) having the sequence of SEQ ID NO. 2 (NH2-NSDSECPLSHDGYCL-HDGVCMYIEALDKYACNCWGYIGERCQYRDLKWW ELR-COOH), and a second polypeptide of an authentic basic fibroblast growth factor (bFGF) having the sequence of SEQ ID NO. 1 (NH$_2$PALPEDGGSG$^{10}$AFPPGHFKDP$^{20}$KRLYCKNG GF$^{30}$FLRIHPDGRV$^{40}$DG VREKSDPH$^{50}$IKLQLQAEER$^{60}$GWSIKGVCA$^{70}$NRY LAMKED$^{80}$GRLLASKCV T$^{90}$DECFFFERLE$^{100}$SNNYNTYRSR$^{110}$KYTSWYVA LK$^{120}$RTGQYKLGSK$^{130}$T GPGQKAILFL$^{140}$PMSAKS-COOH), wherein the DNA construct comprises an insert consisting of, in the order of, an expression cassette, a DNA coding sequence for the first polypeptide, a first intein sequence, a first copy of a DNA coding sequence for the second polypeptide, a second intein sequence, and a second copy of DNA coding sequence for the second polypeptide.

According to a second aspect of the invention, there is provided a DNA construct for use in a *Escherichia coli* host for production of at least a first polypeptide of an authentic human epidermal growth factor (EGF) having the sequence of SEQ ID NO. 2 (NH2-NSDSECPLSHDGYCL-MYIEALDKYACNCWGYIGERCQYRDLKWW ELR-COOH) and a second polypeptide of an authentic basic fibroblast growth factor (bFGF) having the sequence of SEQ ID NO. 1 (NH$_2$PALPEDGGSG$^{10}$AFPPGHFKDP$^{20}$KRLYCKNGG F$^{30}$FLRIHPDGRV$^{40}$DG VREKSDPH$^{50}$IKLQLQAEER$^{60}$GWSIKGVCA$^{70}$NRYL AMKED$^{80}$GRLLASKCV T$^{90}$DECFFFERLE$^{100}$SNNYNTYRSR$^{110}$KYTSWYVAL K$^{120}$RTGQYKLGSK$^{130}$T GPGQKAILFL$^{140}$PMSAKS-COOH), wherein the DNA construct comprises an insert consisting of, in the order of, an expression cassette, an ompA leader sequence, a DNA coding sequence for the first polypeptide, a first intein sequence, a first copy of a DNA coding sequence for the second polypeptide, a second intein sequence, and a second copy of the DNA coding sequence for the second polypeptide.

According to a third aspect of the present invention, there is provided a DNA construct for use in a *Escherichia coli* host for production of at least a first polypeptide of an authentic human epidermal growth factor (EGF) having the sequence of SEQ ID NO. 2 (NH2-NSDSECPLSHDGYCL-HDGVCMYIEALDKYACNCWGYIGERCQYRDLKWW ELR-COOH) and a second polypeptide of an authentic basic fibroblast growth factor (bFGF) having the sequence of SEQ ID NO. 1 (NH$_2$PALPEDGGSG$^{10}$AFPPGHFKDP$^{20}$KRLYCKNG GF$^{130}$ FLRIHPDGRV$^{140}$DG VREKSDPH$^{50}$IKLQLQAEER$^{60}$GWSIKGVCA$^{70}$NRYL AMKED$^{80}$GRLLASKCV T$^{90}$DECFFFERLE$^{100}$SNNYNTYRSR$^{110}$KYTSWYVAL K$^{120}$RTGQYKLGSK$^{130}$T GPGQKAILFL$^{140}$PMSAKS-COOH), wherein the DNA construct comprises an insert consisting of, in the order of, an expression cassette, a DNA coding sequence for the first polypeptide, a first intein sequence and a DNA coding sequence for the second polypeptide.

According to a fourth aspect of the present invention, there is provided a DNA construct for use in a *Escherichia coli* host for production of at least a first polypeptide of an authentic human epidermal growth factor (EGF) having the sequence of SEQ ID NO. 2 (NH2-NSDSECPLSHDGYCL-HDGVCMYIEALDKYACNCWGYIGERCQYRDLKWW ELR-COOH) and a second polypeptide of an authentic basic fibroblast growth factor (bFGF) having the sequence of SEQ ID NO. 1 (NH$_2$PALPEDGGSG$^{10}$AFPPGHFKDP$^{20}$KRLYCKNG GF$^{30}$FLRIHPDGRV$^{40}$DG VREKSDPH$^{50}$IKLQLQAEER$^{60}$GWSIKGVCA$^{70}$NRYL AMKED$^{80}$GRLLASKCV T$^{90}$DECFFFERLE$^{100}$SNNYNTYRSR$^{110}$KYTSWYVA LK$^{120}$RTGQYKLGSK$^{130}$T GPGQKAILFL$^{140}$PMSAKS-COOH), wherein the DNA construct comprises an insert including, in the order of, an expression cassette, a DNA coding sequence for the first polypeptide, a first intein sequence, a first copy of a DNA coding sequence for the second polypeptide, a second intein sequence, and a second copy of DNA coding sequence for the second polypeptide.

According to a fifth aspect of the present invention, there is provided a DNA construct for use in a *Escherichia coli* host for production of at least a first polypeptide of an authentic human epidermal growth factor (EGF) having the sequence of SEQ ID NO. 2 (NH2-NSDSECPLSHDGYCL-HDGVCMYIEALDKYACNCWGYIGERCQYRDLKWW ELR-COOH) and a second polypeptide of an authentic basic fibroblast growth factor (bFGF) having the sequence of SEQ ID NO. 1 (NH$_2$PALPEDGGSG$^{110}$AFPPGHFKDP$^{120}$KRLYCKNG GF$^{130}$FLRIHPDGRV$^{140}$DG VREKSDPH$^{150}$IKLQLQAEER$^{160}$GWSIKGVCA$^{170}$NRYL AMKED$^{180}$GRLLASKCV T$^{190}$ DECFFFERLE$^{100}$SNNYNTYRSR$^{110}$KYTSWYVAL K$^{120}$RTGQYKLGSK$^{130}$T GPGQKAILFL$^{140}$PMSAKS-COOH), wherein the DNA construct comprises an insert including, in the order of, an expression cassette, an ompA leader sequence, a DNA coding sequence for the first polypeptide, a first intein sequence, a first copy of a DNA coding sequence for the second polypeptide, a second intein sequence, and a second copy of the DNA coding sequence for the second polypeptide.

According to a sixth aspect of the present invention, there is provided a DNA construct for use in a *Escherichia coli* host for production of at least a first polypeptide of an authentic human epidermal growth factor (EGF) having the sequence of SEQ ID NO. 2 (NH2-NSDSECPLSHDGYCL-HDGVCMYIEALDKYACNCWGYIGERCQYRDLKWW ELR-COOH) and a second polypeptide of an authentic basic fibroblast growth factor (bFGF) having the sequence of SEQ ID NO. 1 (NH$_2$PALPEDGGSG$^{110}$AFPPGHFKDP$^{120}$KRLYCKNG GF$^{130}$FLRIHPDGRV$^{140}$DG VREKSDPH$^{150}$IKLQLQAEER$^{160}$GWSIKGVCA$^{170}$NRYL AMKED$^{180}$GRLLASKCV T$^{190}$DECFFFERLE$^{100}$SNNYNTYRSR$^{110}$KYTSWYVA LK$^{120}$RTGQYKLGSK$^{130}$T GPGQKAILFL$^{140}$PMSAKS-COOH), wherein the DNA construct comprises an insert including, in the order of, an expression cassette, a DNA coding sequence for the first polypeptide, a first intein sequence and a DNA coding sequence for the second polypeptide.

Preferably, the DNA construct may be devoid of an ompA leader sequence. Alternatively, the DNA construct may comprise an ompA leader sequence between the expression cassette and the DNA coding sequence for the first polypeptide, and a second intein sequence after the DNA coding sequence for the first polypeptide, and a second copy of DNA coding sequence for the second polypeptide after the second intein sequence.

In an embodiment, the DNA construct may be devoid of an ompA leader sequence between the expression cassette and the DNA coding sequence for the first polypeptide, but comprising a second intein sequence after the DNA coding sequence for the first polypeptide, and a second copy of DNA coding sequence for the second polypeptide after the second intein sequence.

The intein sequences may be *Saccharomyces cerevisiae* vascular membrane ATPase (VMA).

According to a seventh aspect of the present invention, there is provided an engineering biological system, comprising a DNA construct as described above, and the system may be an *Escherichia coli* host.

According to an eighth aspect of the present inventing, there is provided a method of producing authentic basic fibroblast (bFGF), comprising a step of introducing a DNA construct as described above, or cultivating an engineering biological system as described above.

Preferably, the cultivating may be performed in a fermentation culture of a fed-batch system.

Suitably, the method may be devoid of using Isopropyl β-D-1-thiogalactopyranoside (IPTG) for induction.

Advantageously, duration of feeding or glucose feeding to the fed-batch system may be up to 6 hours.

In one embodiment, the feeding may commence at the *Escherichia coli* host's early log-growth phase and be stopped when the *Escherichia coli* host has reached its stationary phase.

In one embodiment, after feeding the cultivating may be up to 7 hours.

BRIEF DESCRIPTION OF DRAWINGS

Some embodiments of the present invention will now be explained, with reference to the accompanied drawings, in which:—

DETAILED DESCRIPTION OF PREFERRED EMBODIMENTS OF THE INVENTION

Figures 1, 1A, 1B, 1C, 1D:
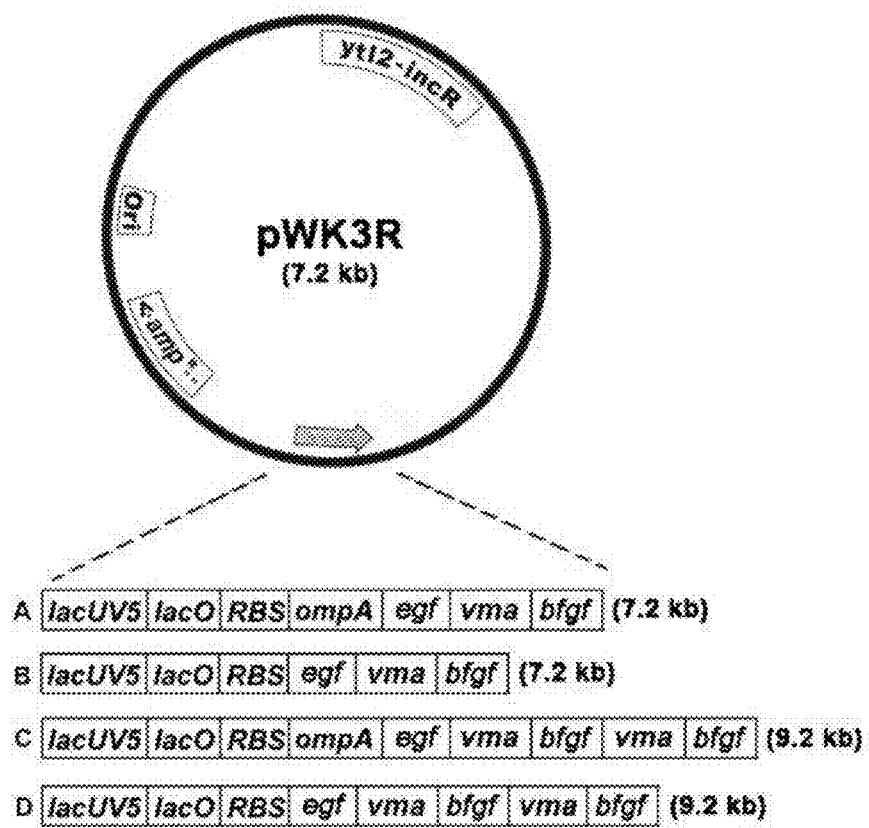
FIG. 1 (plasmid representation) and FIGS. 1A-1D (insert representations) are schematic diagrams showing embodiments of DNA construct according to the present invention, the DNA constructs for use in expressing authentic bFGF (Key: The top diagram shows the parental vector pWK3R, with the hatched arrow representing the genetic elements responsible for bFGF expression. The four constructs: (A) pWK3R, and its three derivatives: (B) pWK3ROmpAd, (C) pWK311R, and (D) pWK311ROmpAd, together with the genetic elements forming their own hatched arrows are specified underneath. Symbols for the components shown in pWK3R and its three derivatives are: ori=origin of replication in *E. coli*; amp$^R$=structural gene conferring resistance to ampicillin; ytl2-incR=ytl2-incR system for plasmid stability of *Salmonella typhimurium*; bfgf=bfgf gene; egf=egf gene; lacUV5=lacUV5 promoter; lacO=lac operator RBS=consensus ribosomal binding site; ompAL=ompA leader sequence; vma=VMA coding sequence. Arrow indicates the direction of transcription. Information in parenthesis indicates the plasmid size)

The versatile physiological functions of bFGF have recently attracted much attention. However, the incredible high prices of bFGF have seriously hindered its availability for wide-scale commercial applications. Moreover, despite the commercial availability of bFGF, very often only structural variants of bFGF instead of the 146 aa authentic product may be procured [1]. Conventional approaches of fusing bFGF with tag proteins or signal peptides have shown to be difficult in yielding the authentic 146 aa polypeptide.

The present invention employs novel means and methods for amplification of gene expression, for use in hyper-production of authentic human basic fibroblast growth factor (hbFGF).

It is to be noted that the reference of authentic hbFGF in the context of the present invention means the produced hbFGF is not only authentic in terms of the sequence having the exact 146 amino acids of the native hbFGF, it also possesses the same characteristics or configuration of solubility, bioactivity, non-truncation, free of modification at the C- or N-terminal, free of affinity tags, and is secreted/secretable at least to some extent, self-cleavable or cleaved from proteins or other proteins simultaneously produced, as the native hbFGF.

It is also to be noted that the reference to hyper-production in the context of the present invention refers to the level of production more than at least twice of the expected level, or more than thrice of the expected level. In a preferred embodiment of the present invention, the level of hyper-production is six times of the expected level.

Specifically, compared to the use of a DNA expression construct pWK3R, when an embodiment of an improved DNA construct of the present invention is used there is an unexpected increase in level of production of the authentic human basic fibroblast growth factor. (The improved DNA construct will be discussed below in this description.) When a refined fed-batch fermentation protocol is also adopted, the novel method can achieve a phenomenal and unexpected yield of 610 mg/L of the 146 aa with SEQ ID NO. 1 (NH$_2$PALPEDGGSG$^{110}$AFPPGHFKDP$^{120}$KRLYCKNGG F$^{130}$FLRIHPDGRV$^{140}$DG VREKSDPH$^{150}$IKLQLQAEER$^{160}$GWSIKGVCA$^{170}$NRYL AMKED$^{180}$GRLLASKCV T$^{190}$DECFFFERLE$^{100}$SNNYNTYRSR$^{110}$KYTSWYV ALK$^{120}$RTGQYKLGSK$^{130}$T GPGQKAILFL$^{140}$PMSAKS-COOH) authentic human basic fibroblast growth factor (bFGF) in *Escherichia coli*. Please also see Appendix. (The refined fed-batch fermentation protocol will be discussed below in this application.) This is to be contrasted with when using a prior version of DNA construct and production protocol only about 100 mg/L was yielded. In other words, there is not just an increase of production level of two times or three times, but over six times. This increase of production level satisfies the definition of hyper-production in the context of the present invention. It is to be noted that there is a simultaneous production of authentic EFG. In an embodiment, the level of EGF production is at an unexpected level of substantially 74 mgL$^{-1}$.

Studies show that with the improved DNA construct a majority of the bFGF was produced intracellular in the cytoplasm of the *E. coli* host, although in an experiment a small amount (~18%) of the bFGF was found extracellularly in the supernatant. In an experiment in which a concentration of about 610 mg/L was yielded, about 510 mg/L was found intracellularly and about 109 mg/L was found extracellularly. Nevertheless, it was ascertained that regardless of the source both intracellularly and extracellularly bFGF produced was found to be authentic and functional with full potency. The meaning of authenticity in the context of the present invention has been discussed above.

As preliminary discussion, experiments conducted leading to the present invention showed that the DNA construct pWK3R was first modified to form plasmid pWK311 ROmpAd, which was devoid of the ompA leader sequence and possessed two copies of a DNA segment encoding a fusion product comprising an intein, *Saccharomyces cerevisiae* vascular membrane ATPase (VMA), and bFGF. When *E. coli* transformant JM101 [pWK311ROmpAd] was cultivated using a refined fed-batch fermentation protocol, superb expression resulting in a total yield of 610 mg/L of bFGF was detected. Despite existing in high levels, the bFGF remained to be soluble and with the same level of bioactivity of the native hbFGF.

Further details including experimental data of the present invention are discussed as follows.

Strategy for Enhancing Expression of Recombinant bFGF

The present invention began by employing a human epidermal growth factor (EGF) excretion plasmid, pWKW2, and the coding sequence for an intein, *Saccharomyces cerevisiae* vascular membrane ATPase (VMA). Then, an expression construct, pWK3R, has been engineered to achieve co-expression of authentic EGF and human basic fibroblast growth factor (bFGF) in *E. coli*. Please see FIG. 1.

The present invention enhances the expression of bFGF through a systematic approach involving two steps: first, by genetic modifications of pWK3R to delete the ompA leader sequence, and applying a novel amplification method, to achieve a two-fold increase in the copy number of the bfgf gene; and second, to further enhance the productivity of an optimized transformant expressing bFGF, employing a refined fed-batch fermentation protocol.

Engineering of DNA Constructs Expressing bFGF

Essentially, two different genetic modifications were performed on pWK3R (FIG. 1A) to result in three plasmid derivatives: pWK3ROmpAd, pWK311R and pWK311ROmpAd (FIG. 1). In constructs pWK3ROmpAd and pWK311ROmpAd, the ompA leader originally carried on pWK3R was deleted. One major difference between these two derivatives was that pWK311 ROmpAd (FIG. 1D) carried two copies of a DNA fusion product formed between the VMA coding sequence (vma) and the bfgf gene, whereas pWK3ROmpAd (FIG. 1B) had only one copy of the DNA fusion concerned. On the other hand, similar to pWK311ROmpAd (FIG. 1D), pWK311R (FIG. 1C) was also modified to contain two copies of the mentioned DNA fusion. However, it retained the ompA leader, thus enabling also secretory, in addition to intracellular, production of both EGF and bFGF.

Time Course Studies

Expression of bFGF in *E. coli* JM101 transformants harboring the four plasmids: pWK3R, pWK3ROmpAd, pWK311R and pWK311ROmpAd (FIG. 1) was first compared in shake flasks under IPTG induction. Western blot analysis of culture samples revealed that in addition to JM101 [pWK3R], which was capable of producing bFGF as reported previously[9], the other three transformants were also able to express bFGF as a fully processed protein (Table 2). The results support the conclusion that the precursor/intermediate products, including EGF-VMA-bFGF, OmpA-EGF-VMA-bFGF-VMA-bFGF, OmpA-EGF-VMA-bFGF and EGF-VMA-bFGF-VMA-bFGF, which were initially expressed in the three transformants harboring the construct derivatives, were able to undergo auto-cleavable activities to yield bFGF (Table 2), with the developments similar to that observed previously in transformant JM101 [pWK3R].

Figure 2:
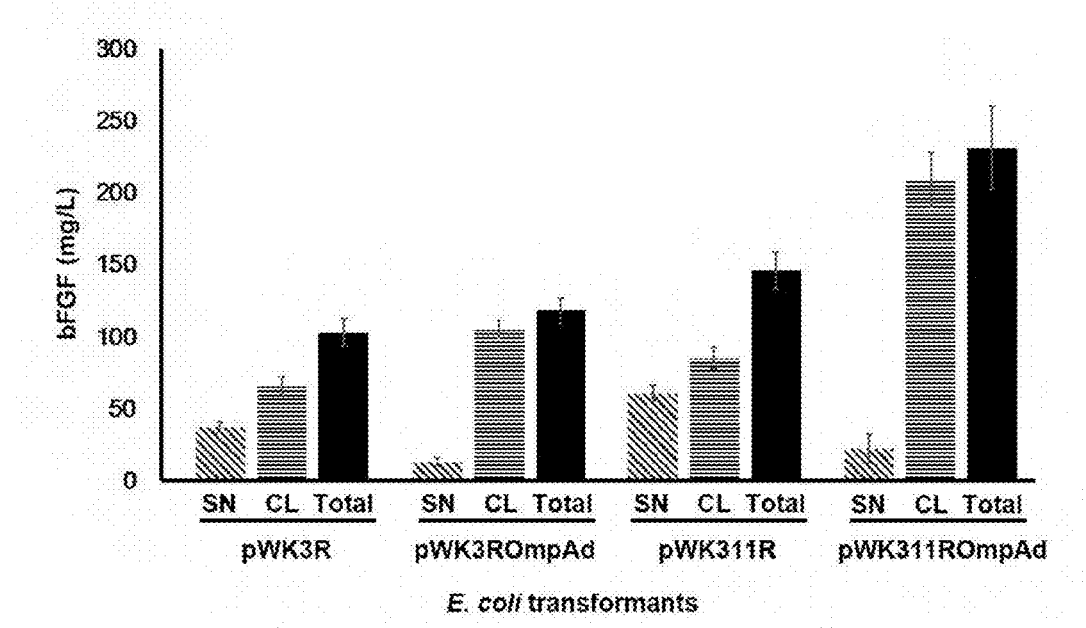
FIG. 2 is a graph showing production level of authentic bFGF from the use of the DNA constructs of FIG. 1 transformed in *E. coli* (Key: *E. coli* transformants harboring the four constructs as indicated beneath the x-axis were grown in shake flasks as described in Methods. The cultures were fractionated into culture supernatant (SN) and cell lysate (CL) samples, which were then assayed by western blot analysis, followed by quantification of bFGF. Each experiment was repeated three times and standard error bars are shown)

Despite employing the same regulatory controls and intein, VMA, the four constructs resulted in noticeable difference in the level of bFGF expression (FIG. 2). The results revealed that the three plasmid derivatives were more efficient than pWK3R in expressing bFGF (FIG. 2). The improvements were likely attributable to a two-fold increase in the copy number of the bfgf gene, in particular when constructs pWK311R and pWK311ROmpAd (FIG. 1) were considered. Their levels of bFGF expression were significantly higher than that resulting from pWK3R (FIG. 2).

On the other hand, deletion of the OmpA signal peptide from the precursor products was notably beneficial to the overall expression of bFGF. Without the signal peptide, essentially all resources for bFGF production would be confined in the cytoplasm, as in the case of JM101 [pWK3ROmpAd] and JM101 [pWK311ROmpAd], thereby providing higher yields of bFGF than their respective counterparts, JM101 [pWK3R] and JM101 [pWK311R] (FIG. 2), in which their constructs contained the ompA leader (FIG. 1).

Primary Structure of bFGF Expressed in E. coli Tranformants Harboring the Four Constructs The primary structure of bFGF purified from the culture media and cell lysates of E. coli transformants harboring pWK3R, pWK3ROmpAd, pWK311R and pWK311ROmpAd was determined as previously reported[9]. Sequencing results confirmed that both the supernatant and cytoplasmic bFGF samples purified from the cultures of the four transformants contained the correct N- and C-termini (Table 2), supporting the conclusion that the bFGF samples comprised 146 aa residues, with the same composition as that of native bFGF. Another noteworthy point concerns the homogeneity of bFGF resulting from the expression of constructs pWK311R (FIG. 1C) and pWK311ROmpAd (FIG. 1D), each of which possessed two copies of the bfgf gene fused with two copies of vma to form a DNA fusion: vma/bfgf/vma/bfgf. Although the leftward bfgf gene in both of the constructs concerned was flanked by two copies of vma, aa composition analysis revealed the presence of a homogeneous set of tryptic peptides derived from the hydrolysis of bFGF (Table 2). The results support the conclusion that irrespective of whether bFGF is fused at either the N- or C-terminus of VMA, intriguingly, the cleavage at either junction is precisely accomplished as desired to yield the authentic product.

Activities of bFGF Expressed by Constructs pWK3ROmpAd, pWK311R and pWK311ROmpAd

Figure 5:
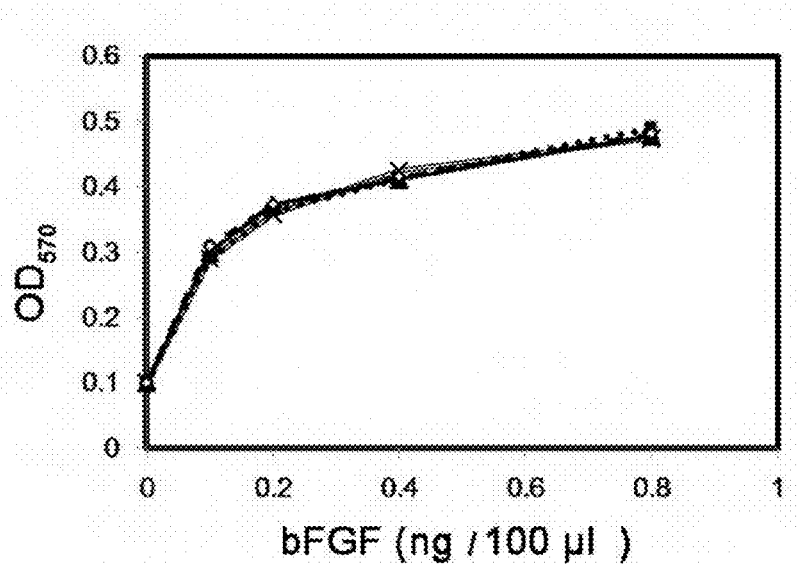
FIG. 5 is graph showing bioassays of bFGF produced by three transformants used in the experiments.

Purified bFGF from both culture media and lysates of transformants JM101 [pWK3ROmpAd], JM101 [pWK311R] and JM101 [pWK311ROmpAd] were assayed for mitogenic activities performed as described previously[9]. The results revealed that all bFGF samples were as potent as that of the authentic standard (FIG. 5), supporting the fact that bFGF detected in either the cytoplasm or the culture media of all three transformants are fully bioactive. FIG. 5 is a graph showing Samples of bFGF were purified from IPTG induced cultures of JM101[pWK3ROmpAd], JM101 [pWK311R] and JM101[pWK311 ROmpAd]. The assays for mitogenic effects of bFGF on the proliferation of BALB/C 3T3 fibroblast cells were described in Methods. The bioactivities of standard bFGF (═X═), JM101 [pWK3ROmpAd] (-▲-), JM101[pWK311R] (---◇---) and JM101[pWK311ROmpAd] (••••■••••) are shown. The comparison shows that the bioactivities of the three recombinant bFGF samples and standard bFGF form a superimposed line, supporting that their bioactivities share the same potency.

Fermentative Production of bFGF

Among the four constructs studied, pWK311ROmpAd provided the best performance in bFGF expression (FIG. 2). Therefore, the ability of JM101 [pWK311ROmpAd] to express bFGF using a modified protocol of the fed-batch fermentation process with continuous glucose feeding developed previously for EGF expression was investigated. However, there were two distinct differences between the current approach and that reported previously[15]. First, IPTG induction was excluded. This was counter intuitive because in the past IPTG was considered and used to increase efficiency of transcription thus to enhancing gene expression of production of the target protein. Second, the duration of feeding was reduced from the formerly reported 9 h to 6 h in this study. This was also counter intuitive because longer feeding time was considered to allow more time for nutrient supply thus to increase gene expression or target protein production. Moreover, after feeding, the cultivation was allowed to continue for 7 more h prior to harvesting (Methods).

Figure 3A:
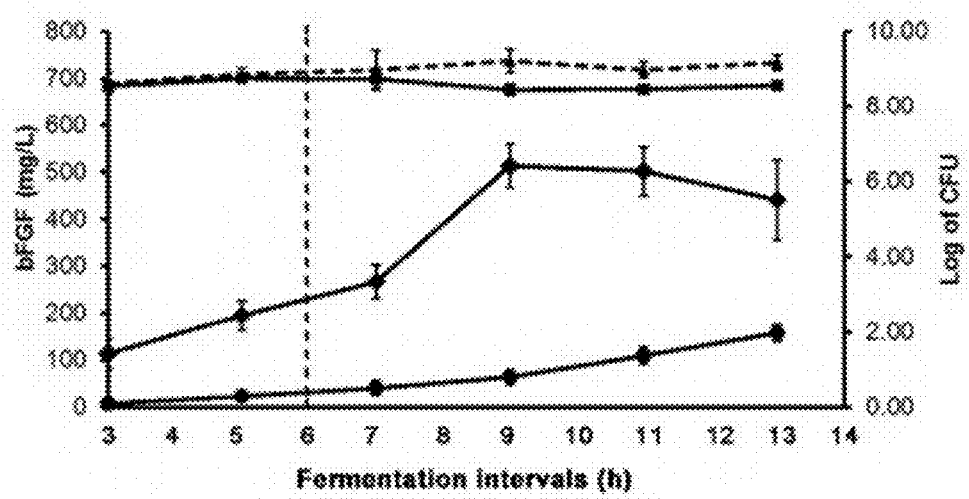
FIG. 3A and FIG. 3B are graphs showing expression of bFGF by transformants JM101 [pWK311ROmpAd] and JM101 [pWK3R] cultivated in a small-scale fermentor under fed-batch conditions without induction.
Figure 3B:
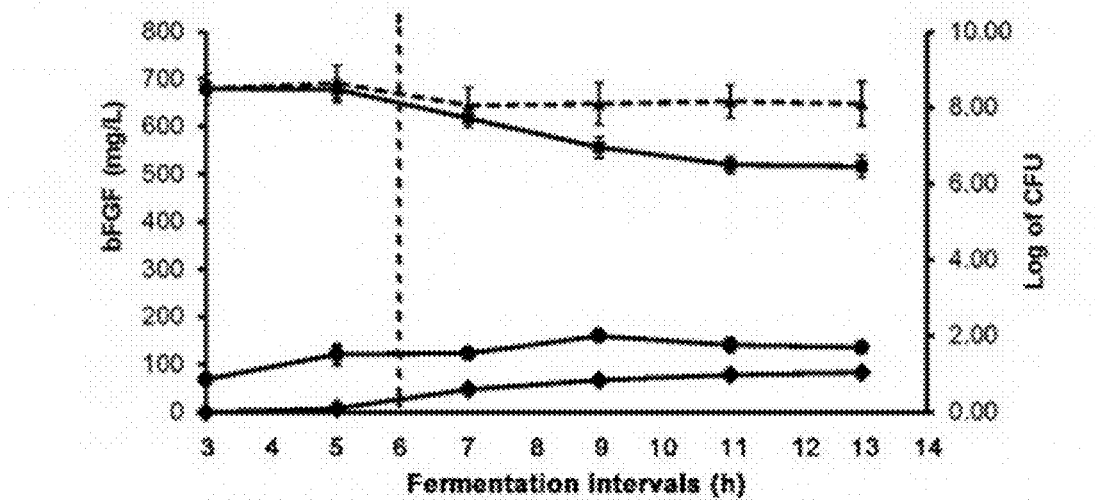
Figure 4:
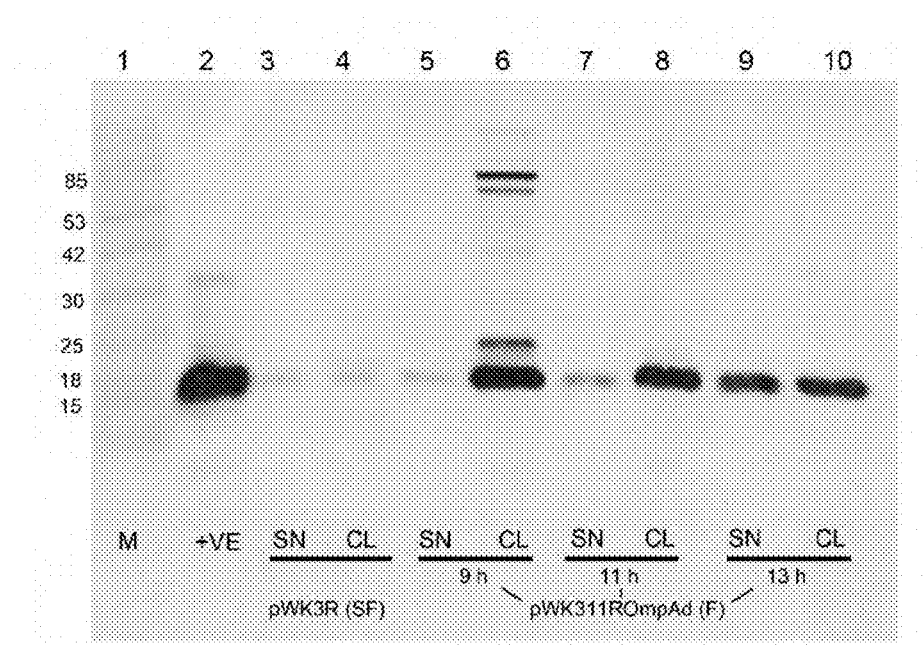
FIG. 4 is an image showing a Western blot analysis of bFGF expressed by transformants JM101 [pWK3R] and JM101 [pWK3ROmpAd] grown under shake flask and fermentation conditions (Key: Shake flask (SF) and fermentation (F) conditions for growth of JM101 [pWK3R] and JM101 [pWK311 ROmpAd], respectively, are described in Methods. Culture supernatant (SN) and cell lysate (CL) samples were prepared from the former (lanes 3-4) and latter (lanes 5-10) cultures and analyzed for bFGF activities by western blotting. The amounts of SN and CL samples loaded were equivalent to 6 µl and 2.5 µl of each culture, respectively. The constructs concerned are indicated beneath the blot. The three time points: 9 h, 11 h and 13 h, at which samples collected from the JM101 [pWK311ROmpAd] culture are denoted. Other symbols used are: M=protein markers (lane 1) in kDa; +VE=bFGF standard (lane 2))

Referring to FIGS. 3A & 3B, culture samples of (A) JM101 [pWK311ROmpAd] and (B) JM101 [pWK3R] were taken at different time points from the fermentor and viabilities of plasmid-free and plasmid containing cells were determined on plain agar plates (---▲---) and agar plates supplemented with ampicillin (-■-), respectively. CFU refers to colony forming units. Levels of bFGF detected in the cell lysate (-◆-) and culture supernatant samples (—•—) are presented. The fermentation intervals present developments of cell growth and bFGF expression during two different stages of cultivation (partitioned by the vertical dotted line): last phase of glucose feeding (3-6 h) and the "pending period" (6-13 h). Each growth experiment of the two transformants was repeated three times and standard error bars are shown. Glucose feeding was commenced at early log-growth phase and was stopped after cell growth had reached the stationary phase, during which production of bFGF was maximum (FIG. 3A) and yields of extracellular bFGF, resulting presumably from minor cell lysis, increased progressively (FIG. 3A and FIG. 4). During the last 7 h of cultivation, designated the "pending period", the productivities of bFGF were obviously far better than those detected at earlier time points (FIG. 3A).

Surprisingly, the modified protocol was shown to be highly rewardable to result in a final yield of as high as 610 mg/L of bFGF, e.g., at 5 h after entering the "pending period" (FIG. 3A), which was 1.6 times higher than that derived from the same transformant grown in shake flasks (FIG. 2). The high levels of bFGF expressed did not seem to impose obvious harmful effect on either cell growth or the quality of bFGF, which remained soluble and bioactive (FIG. 5) throughout the fermentation process (FIG. 3A). During the "pending period", bFGF was progressively released from the lysed cells to the culture medium. The supernatant samples collected at latter time points were shown to provide an impressive source of bFGF, in terms of not only quantity [representing about one-fifth of the overall bFGF yield (FIG. 2 and FIG. 3A)], but also quality, which contained comparatively "purer" bFGF with lower levels of host cell protein contamination.

Despite employing the refined fermentation protocol, JM101 [pWK3R] (FIG. 3B) did not obtain the same extent of improvement in total bFGF yield as that shown by JM101 [pWK311ROmpAd] (FIG. 3A). Apparently, only one copy of the bfgf gene harbored by pWK3R and low cell viabilities of JM101 [pWK3R](FIG. 3B), which were 100 times lower than those of JM101 [pWK311ROmpAd] at later growth points (FIG. 3A), significantly affected the performance of JM101 [pWK3R] in bFGF expression. Although the highest total yield of JM101 [pWK3R] upon fermentation was over 200 mg/ml (FIG. 3B), which was 2 times higher than the same clone grown in shake flasks (FIG. 2), the level was 3 times lower than that of JM101 [pWK311ROmpAd] grown under the same fermentative conditions (FIG. 3A).

In the course leading to the present invention, despite a variety of possible microbial systems which could be tried for production of useful recombinant proteins, the inventors have determined that E. coli is to be used for the expression of pharmaceutically important proteins, including a wide range of growth hormones and factors. Applying both excretion and intein-mediated expression systems, the inventors have unexpectedly achieved recombinant simultaneous production of two important skin growth factors, EGF and bFGF, as authentic proteins in E. coli[9]. Interestingly, using the latter approach, both independent and cleaved EGF and bFGF were detected not only in the culture medium, but also in the cytoplasm. Moreover, since both EGF and bFGF were identified as precisely processed products detached from their fusion intein partner, VMA, the results support the interpretation that their precursors/intermediates existed likely in soluble forms, which remained auto-cleavable to yield EGF and bFGF. The same approach has also been employed for co-expression and auto- or self-cleavages of fusion products formed between different inteins and widely dissimilar proteins. The products were also found to be free from undesirable modification at the C- or N-terminal, or truncation.

During the course of the present invention of producing authentic bFGF, the inventors had also investigated the effects of two structural modifications: (i) deletion of the ompA leader sequence, and (ii) doubling the copy number of the DNA fusion formed between vma and the bfgf gene, on improving bFGF expression. It was unexpectedly found that both changes had a positive impact on the production of bFGF (FIG. 2). Moreover, when the two modifications were both introduced into pWK311ROmpAd (FIG. 1), the changes resulted in a much better yield of bFGF (FIG. 2). This is unexpected because conventionally the use of the ompA leader sequence was considered as essential as far as effecting excretion or secretion is concerned. The attempt of doing away with the ompA leader sequence still allows the excretion or secretion.

The outcomes support the following conclusions. First, two copies of the bfgf gene yielded better bFGF expression than did one copy. This is counter intuitive and unexpected in three aspects. With the two copies, the increase in yield is not just twice as much, but more than six times. Further, conventionally, there were studies showing that excessive inducement of protein production would cause "choking" to the cell and cause death. However, with the DNA construct taught in the present invention, not only there was not cell choking or death, the production level is hyper-produced. The meaning of "hyper-production" has been discussed earlier on in this description.

Figure 6:
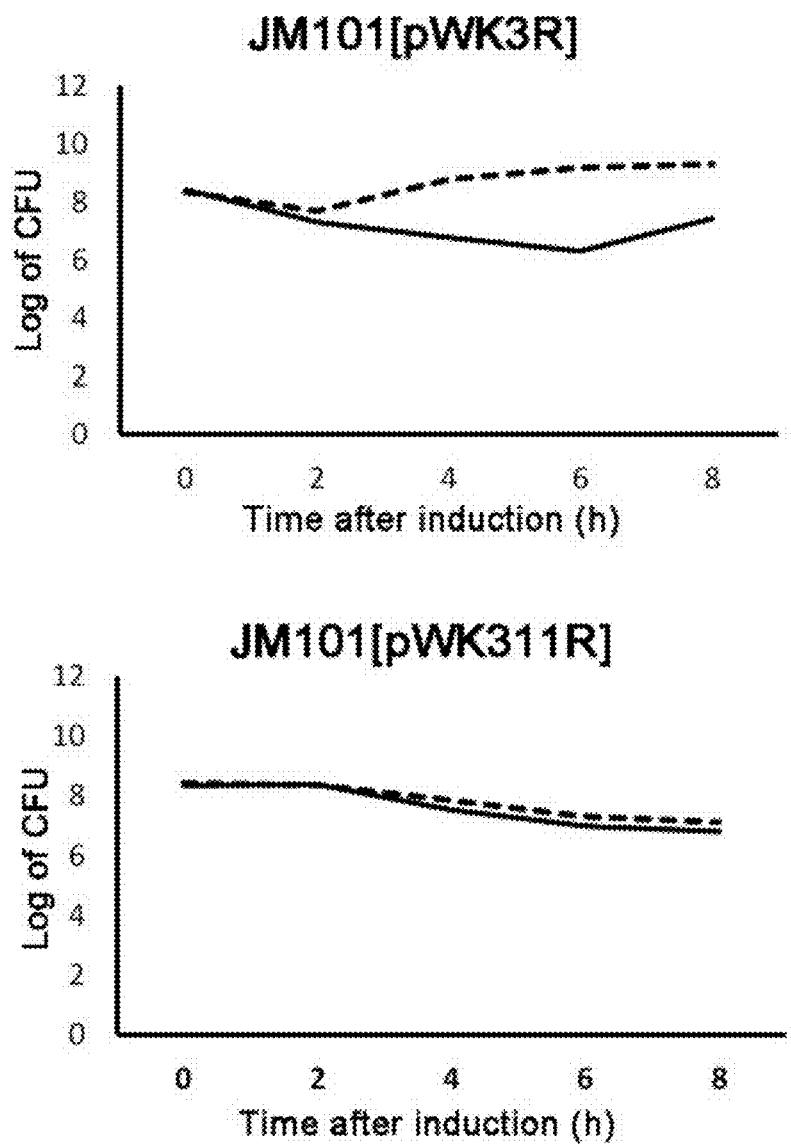
FIG. 6 are graphs showing viable cells counts obtained from the time course study of various *E. coli* cultures.
Figure 6:
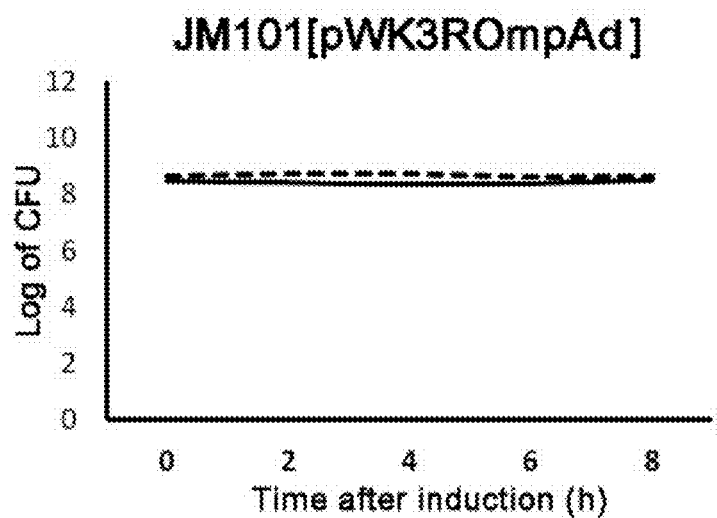
Figure 6:
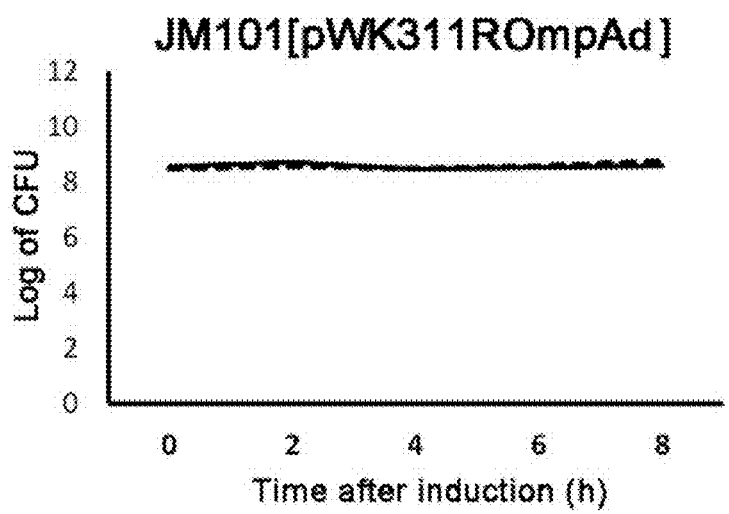

Second, deletion of the ompA leader sequence from constructs pWK3ROmpAd and pWK311ROmpAd (FIG. 1) resulted in improved cell viabilities of their transformants in shake flasks (FIG. 6). This notion is supported from the findings that pWK3R, which contained the ompA leader sequence (FIG. 1), elicited high plasmid instabilities and low cell viabilities in JM101 [pWK3R] (FIG. 3B), despite the growth of JM101 [pWK3R] carried out under optimized fermentative conditions (FIG. 3B). However, [pWK311ROmpAd], in which ompA was deleted, grew with much higher plasmid stabilities and cell viabilities under the same conditions (FIG. 3A). These observations were in line with our previous findings that secretory production of recombinant proteins in E. coli would cause detrimental, and even lethal, effects on the host cells[16,26,27]. As expected, deletion of the ompA leader sequence from constructs pWK3ROmpAd and pWK311ROmpAd (FIG. 1) resulted in improved cell viabilities of their transformants (FIG. 3A). Nonetheless, deletion of the OmpA signal hampered secretion of bFGF, thus resulting in essentially cytoplasmic production of the polypeptide, and hence higher yields of intracellular, or overall, bFGF (FIG. 2). Therefore, possessing both structural modifications, pWK311ROmpAd was revealed to be the most productive construct which was 50-100% more potent than the other three plasmids in bFGF expression (FIG. 2)

Third, while the two copies of bfgf gene in the DNA construct are identical, they are configured differently in that their adjacent elements are different. Specifically, one copy is sandwiched by two intein sequences while the other copy is not. Prior studies indicated that this configuration would cause the protein produced from one of the copies different (i.e. undersirably modified) from the authentic protein.

The rewarding achievement of pWK311ROmpAd in small scale studies prompted us to investigate its performance in fermenter cultivation. We adapted a glucose feeding fed-batch approach previously employed to yield high levels of EGF in E. coli, with the following modifications. First, IPTG induction was excluded in growing JM101 [pWK311ROmpAd] since high efficiencies of transcription of heterologous genes might seriously retard cell growth. Second, a shortened, 6 h instead of the previously reported 9 h, glucose feeding regime was adopted. Despite using a significantly shorter feeding time, the rate of cell growth was shown to be normal and remained high at a cell density of over $10^8$ cells/ml (FIG. 3A). Obviously, the non-induced conditions offered a favorable instead of a harmful environment for JM101 [pWK311ROmpAd] to grow. Another point supporting this notion was that pWK311ROmpAd was maintained quite stably in its host during growth (FIG. 3A). Otherwise, if bFGF were expressed under IPTG induction, pWK311ROmpAd could have suffered serious instability, as reported previously in studies where other recombinant proteins were expressed under induction.

Although pWK311ROmpAd was devoid of the ompA leader, as a result of cell lysis, high levels of bFGF, reaching 110 mg/L, were released to the culture medium at the latter time points of the "pending period" (FIG. 3A). This concentration, representing one-fifth of the maximum production of bFGF obtainable from JM101 [pWK311ROmpAd], provided a convenient source of less contaminated bFGF. It was previously postulated that high levels of recombinant proteins present in E. coli might weaken its membrane structure, thus resulting in increased susceptibility to cell lysis. It will be interesting to explore whether bFGF release may be enhanced with further improvement in the overall expression of the peptide or modulations of the glucose feeding program including the duration of the "pending period".

The application of the novel approach of gene amplification, as illustrated by the bfgf/vma/bfgf gene fusion engineered in constructs pWK311R (FIG. 1C) and pWK311ROmpAd (FIG. 1D), is well demonstrated in this report to result in not only better yields but also a homogeneous preparation of bFGF (Table 2). Employing the optimized intein-mediated expression approach, together with a refined, non-induced, fed-batch fermentation protocol, we have been successful in achieving a phenomenal yield of 610 mg/L of bFGF in *E. coli*. Further optimization of both the expression and fermentation conditions may not only enable operations to be performed cost-effectively on a large scale, but may also facilitate efficient production of a wide collection of both intracellular and secretory proteins.

More details regarding experiments leading to the present invention are as follows.

Methods

Bacterial Strain & Chemicals

*E. coli* strain JM101 was the host employed in this study. The Phusion PCR kit, restriction, and modifying enzymes were purchased from New England Biolabs (Ipswich, Mass., USA). All oligos were purchased from Invitrogen (Carlsbad, Calif., USA). Other chemicals were purchased from Sigma-Aldrich Corporation (St. Louis, Mo., USA) unless otherwise specified. Antibodies against bFGF were raised in rabbits.

Construction of Expression Constructs

Plasmids pWK311R and pWK3ROmpAd were derived from pWK3R, with the following modifications. The EcoRI-SphI fragment of pWK3R was replaced, by a PCR fragment formed using primers P5-P8 (Table 1), which was composed of the following components: lacUV5 promoter, lac operator (lacO), ribosomal binding site (RBS), and egf gene to form pWK3ROmpAd. Another PCR fragment, Fragment A, synthesized using primers P1-P4 (Table 1), containing the bfgf gene fused with the VMA coding sequence (vma), was inserted into the BamHI site of pWK3R to form pWK311R. Lastly, to develop pWK311ROmpAd, Fragment A was inserted into the BamHI site of pWK3ROmpAd.

Shake Flask Cultivations

*E. coli* transformants were grown at 34° C. in MMBL medium supplemented with 70 μg/ml of ampicillin. In time-course experiments, a 250 ml flask containing 50 ml of growth medium was inoculated with a freshly grown colony and shaken at 250 rpm and 34° C. until the culture reached an $A_{550}$ reading of 8.0. Subsequently, a final concentration of 0.1 mM IPTG was added and the culture was continuously grown for 8 h. Then 1 ml of the culture was centrifuged and the SN was saved. The cell pellet was suspended in 120 μl of Tris.HCl buffer (50 mM, pH 8.0), followed by an addition of 83 μl of EDTA solution (0.25 M, pH 8.0). The cell mixture was incubated on ice for 5 min and then treated with 120 μl of lysozyme solution (10 mg/ml) at 37° C. for 20 min. After addition of 83 μl of lysis buffer (10 mM EDTA, 10% Triton X-100, and 50 mM Tris.HCl, pH 8.0), the tube was inverted gently, followed by spinning at 13,000 rpm for 10 min to remove the cell debris. Both the clarified lysate (CL) and culture supernatant (SN) fractions were analyzed for bFGF by Western blot analysis, of which the images were quantified by densitometry using the ImageJ software (National Institutes of Health, USA).

Purification and Analysis of bFGF

The purification of bFGF using heparin-agarose chromatography and analysis of the purified bFGF by liquid chromatography tandem mass spectrometry were described previously.

Biological Assays of bFGF

The mitogenic effects of purified bFGF samples on the proliferation of BALB/C 3T3 fibroblast cells were analyzed by the MTT assay as described previously.

Fermentation

MMBL medium was used throughout the entire fermentation process including the preparation of starter cultures. To begin with, a fresh colony of JM101 [pWK311ROmpAd] was inoculated in 50 ml of MMBL medium supplemented with 70 μg/ml of ampicillin. The cells were grown at 34° C. until an $A_{550}$ reading reached 2.0. Then 15 ml of the starter were added into 135 ml of fresh MMBL medium supplemented with 70 μg/ml of ampicillin, and the culture was grown for 3 h at 34° C. The entire 150 ml culture was then added into a 2 L fermentor containing 1.35 L of fresh MMBL medium. The pH of the culture was maintained at 6.8 using 1M NaOH solution. When the pH began to decrease, the culture was fed with 50% glucose at a rate of 4 ml/h. The pH was maintained at 6.8 until the $A_{550}$ reading was 15.0, which took about 6 h to reach. The feeding process was then stopped, but the operation of the fermentor was allowed to continue for the next 7 h ("pending period"), during which lytic release of bFGF into the medium was expected to occur. Culture samples were collected at different time points of the fermentation process. The fractionated cell pellet and culture supernatant samples were then subjected to various analyses.

It should be understood that certain features of the invention, which are, for clarity, described in the content of separate embodiments or experiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose. Some of this prior art are indicated as follows, and their contents in entirety are incorporated herein.

REFERENCES

1. Bikfalvi, A., Klein, S., Pintucci, G. & Rifkin, D. B. Biological roles of fibroblast growth factor-2. *Endocrine Reviews* 18, 26-45 (1997).
2. Tabata, Y. et al. Bone regeneration by basic fibroblast growth factor complexed with biodegradable hydrogels. *Biomaterials* 19, 807-815 (1998).
3. Sellke, F. W., Laham, R. J., Edelman, E. R., Pearlman, J. D. & Simons, M. Therapeutic angiogenesis with basic fibroblast growth Factor: technique and early results. *The Annals of Thoracic Surgery* 65, 1540-1544 (1998).
4. Andrades, J. A. et al. Production of a recombinant human basic fibroblast growth factor with a collagen binding domain. *Protoplasma* 218, 95-103 (2001).
5. Mu, X. et al. High-level expression, purification, and characterization of recombinant human basic fibroblast growth factor in *Pichia pastoris*. *Protein Expression and Purification* 59, 282-288 (2008).
6. Garke, G., Deckwer, W. D. & Anspach, F. B. Preparative two-step purification of recombinant human basic fibroblast growth factor from high-cell-density cultivation of *Escherichia coli*. *Journal of Chromatography B: Biomedical Sciences and Applications* 737, 25-38 (2000).
7. Alibolandi, M., Mirzahoseini, H., Alibolandi, M. & Mirzahoseini, H. Purification and refolding of overexpressed human basic fibroblast growth factor in *Escherichia coli*. *Biotechnology Research International, Biotechnology Research International* 2011, 2011, e973741 (2011).
8. Cost of Basic fibroblast growth factor|Biocompare.com. Available at: http://www.biocompare.com/Protein-Biochemistry/21932-Proteins-Human-Source/?search=basic+fibroblast+growth+factor. (Accessed: 11th December 2015)
9. Kwong, K. W. Y. & Wong, W. K. R. A revolutionary approach facilitating co-expression of authentic human epidermal growth factor and basic fibroblast growth factor in both cytoplasm and culture medium of *Escherichia coli*. *Appl Microbiol Biotechnol* 1-10 (2013). doi:10.1007/s00253-013-5090-8
10. Kwong, K. W. Y., Ng, K. L., Lam, C. C., Wang, Y. Y. & Wong, W. K. R. Authentic human basic fibroblast growth factor produced by secretion in *Bacillus subtilis*. *Appl Microbiol Biotechnol* 1-9 (2012). doi:10.1007/s00253-012-4592-0
11. Kwong, K. W. Y., Ng, A. K. L. & Wong, W. K. R. Engineering versatile protein expression systems mediated by inteins in *Escherichia coli*. *Appl Microbiol Biotechnol* 1-8 (2015). doi:10.1007/s00253-015-6960-z
12. Wong, W. K. R. & Sutherland, M. L. Excretion of heterologous proteins from *E. coli*. (1997). U.S. Pat. No. 5,646,015.
13. Wong, D. K. H. et al. Extracellular expression of human epidermal growth factor encoded by an *Escherichia coli* K-12 plasmid stabilized by the ytl2-incR system of *Salmonella typhimurium*. *Journal of Industrial Microbiology and Biotechnology* 21, 31-36 (1998).
14. Huang, R. et al. Human epidermal growth factor excreted by recombinant *Escherichia coli* K-12 has the correct N-terminus and is fully bioactive. *Process Biochemistry* 35, 1-5 (1999).
15. Sivakesava, S. et al. Production of excreted human epidermal growth factor (hEGF) by an efficient recombinant *Escherichia coli* system. *Process Biochemistry* 34, 893-900 (1999).
16. Wong, W. K. R., Fu, Z., Wang, Y. Y., Ng, K. L. & Chan, A. K. N. Engineering of efficient *Escherichia coli* excretion systems for the production of heterologous proteins for commercial applications. *Recent Patents on Chemical Engineering* 5, 44-55 (2012).
17. Ng, A. K. L. et al. Enhancement of fish growth employing feed supplemented with recombinant fish growth hormone expressed in *Bacillus subtilis*. *Research Journal of Biotechnology* 11, 1-11 (2016).
18. Li, Y. Self-cleaving fusion tags for recombinant protein production. *Biotechnol Lett* 33, 869-881 (2011).
19. Elleuche, S. & Pöggeler, S. Inteins, valuable genetic elements in molecular biology and biotechnology. *Appl Microbiol Biotechnol* 87, 479-489 (2010).
20. Topilina, N. I. & Mills, K. V. Recent advances in in vivo applications of intein-mediated protein splicing. *Mobile DNA* 5, 5 (2014).
21. Cui, C., Zhao, W., Chen, J., Wang, J. & Li, Q. Elimination of in vivo cleavage between target protein and intein in the intein-mediated protein purification systems. *Protein Expression and Purification* 50, 74-81 (2006).
22. Shokri, A., Sandén, A. & Larsson, G. Cell and process design for targeting of recombinant protein into the culture medium of *Escherichia coli*. *Appl Microbiol Biotechnol* 60, 654-664 (2003).
23. Tsang, M. W., Tsang, K. Y. & Wong, W. K. R. The use of recombinant human epidermal growth factor (rhEGF) in a gentleman with drug-induced Steven Johnson syndrome. *Dermatol. Online J* 10, 25 1-4 (2004).
24. Tsang, M.-W. et al. Human epidermal growth factor enhances healing of diabetic foot ulcers. *Diabetes Care* 26, 1856-61 (2003).
25. Wong, W. K. R. Effective Treatment of an unhealed incision of a diabetic patient with recombinant human epidermal growth factor. *Modern Chemistry & Applications* 3, 4, 1-3 (2015).
26. Fu, Z. B., Ng, K. L., Lam, T. L. & Wong, W. K. R. Cell death caused by hyper-expression of a secretory exoglucanase in *Escherichia coli*. *Protein Expr Purif* 42, 67-77 (2005).
27. Fu, Z. B. et al. A two-stage refinement approach for the enhancement of excretory production of an exoglucanase from *Escherichia coli*. *Protein Expr Purif* 48, 205-14 (2006).
28. Wang, Y. Y. et al. Efficient *Bacillus subtilis* promoters for graded expression of heterologous genes in *Escherichia coli*. *Res J Biotechnol* 5, 5-14 (2010).
29. Lam, T. L., Wong, R. S. C. & Wong, W. K. R. Enhancement of extracellular production of a *Cellulomonas fimi* exoglucanase in *Escherichia coli* by the reduction of promoter strength. *Enzyme and Microbial Technology* 20, 482-488 (1997).

LIST OF ABBREVIATIONS kDa=kilo Dalton
SN=culture medium/supernatant
CL=cell lysate
aa=amino acid
MTT=(3-(4,5-dimethylthiazol-2-yl)-2,5-diphenyltetrazolium bromide)
SEM=Standard error of the mean
bFGF=146 aa authentic human basic fibroblast growth factor
EGF=human epidermal growth factor
VMA=*Saccharomyces cerevisiae* vascular membrane ATPase
vma=VMA coding sequence
OmpA=outer membrane protein A
Tables

TABLE 1

Oligos used in the study

| Primer | SEQ NO. | Sequence<sup>a</sup> |
|---|---|---|
| P1 | 3 | 5'-CACTGAAACGCACTGGGCAG-*TATAAACTT*GGATCC*AA*-3' |
| P2 | 4 | 5'-ACCCTTGGCAAAGCAGCTCTTAGCAGACAT-*TATAA**ACTT*GGATCC*AAACAG*-3' |
| P3 | 5 | 5'-ATGTCTGCTAAGAGCTGCTTTGCCAAGGGT-3' |
| P4 | 6 | 5'-TTTCTGCCCAGGTCCTGTTTT-GGATCCAAGTT-3' |
| P5 | 7 | 5'-ACGAGGCCCTTTCGTCTTCA-AGAATTCGCAT-3' |

TABLE 1-continued

Oligos used in the study

| Primer | SEQ NO. | Sequence[a] |
|---|---|---|
| P6 | 8 | 5'-CAGAGTCACTATTCATAATTTTTC-3' |
| P7 | 9 | 5'-GAAAAAATTATGAATAGTGACTCTG-3' |
| P8 | 10 | 5'-CAACAACACAGTTGCATGCATACTT-3' |

[a]The samples included cell lysates and culture media of both shake flask and fermentative cultures. All four transformants: JM101[pWK3R], JM101[pWK3ROmpAd], JM101[pWK311R] and JM101 [pWK311ROmpAd], were included in shake flask cultures, whereas only JM101 [pWK311ROmpAd] and JM101[pWK3R] were involved in fermentor cultivation.

TABLE 2

Analysis of bFGF, purified from the cell samples of E. coli transformants harboring the four embodiment of plasmid constructs[a] by liquid chromatography tandem mass spectrometry

|  | SEQ NO. | Peptide[b,c] | Mr (Calc)[d] | Mr (Expt)[e] |
|---|---|---|---|---|
| (1)  | 11 | $^{NH2-}$PALPEDGGSG$|^{10}$AFPPGHFK | 1779 | 1779 |
| (2)  | 12 | RLYCKNGGF$|^{30}$FLR | 1529 | 1530 |
| (3)  | 13 | NGGF$|^{30}$FLR | 809 | 808 |
| (4)  | 14 | IHPDGRV$|^{40}$DGVR | 1219 | 1220 |
| (5)  | 15 | EKSDPH$|^{50}$IK | 952 | 952 |
| (6)  | 16 | SDPHIKLQLQAEER$|^{60}$ | 1662 | 1663 |
| (7)  | 17 | $|^{60}$GVVSIKGVCA$|^{70}$NR | 1259 | 1258 |
| (8)  | 18 | YLAMKED$|^{80}$GR | 1081 | 1082 |
| (9)  | 19 | CVT$|^{90}$DECFFFER | 1509 | 1508 |
| (10) | 20 | LE$|^{100}$SNNYNTYR | 1273 | 1272 |
| (11) | 21 | LESNNYNTYR | 1272 | 1273 |
| (12) | 22 | $|^{110}$KYTSWYVALK$|^{120}$ | 1259 | 1258 |
| (13) | 23 | TGQYKLGSK$|^{130}$TGPGQK | 1548 | 1548 |
| (14) | 24 | AILFL$|^{140}$PMSAK | 1090 | 1089 |
| (15) | 25 | $|^{130}$TGPGQKAILFL$|^{140}$PMSAKS | 1744 | 1744 |
| (16) | 26 | AILFL$|^{140}$PMSAKS-$^{COOH}$ | 1176 | 1177 |

[b]Subsequent to trypsin digestion of purified bFGF, a total of 466 peptides were identified by the Mascot search engine.
[c]The availability of mature bFGF sequence in the literature has facilitated the selection and alignment of sequencing results of the trypsin digested peptides (16 of them as revealed in the above Table) to finally obtain a full sequence of the recombinant bFGF as shown below.
NH$_2$PALPEDGGSG$|^{10}$AFPPGHFKDP$|^{20}$KRLYCKNGGF$|^{30}$FLRIHPDGRV$|^{40}$ DGVREKSDPH$|^{50}$IKLQLQAEER$|^{60}$GVVSIKGVCA$|^{70}$NRYLAMKED$|^{80}$ GRLLASKCVT$|^{90}$DECFFFERLE$|^{100}$SNNYNTYRSR$|^{110}$KYTSWYVALK$|^{120}$ RTGQYKLGSK$|^{130}$TGPGQKAILFL$|^{140}$PMSAKS-COOH
[d]Theoretical mass-to-charge ratio of the peptide
[e]The experimental mass-to-charge ratio of the peptide

APPENDIX

SEQ ID NO. 1:
NH$_2$PALPEDGGSG$|^{10}$AFPPGHFKDP$|^{20}$KRLYCKNGGF$|^{30}$FLRIHPDGR V$|^{40}$DGVREKSDPH$|^{50}$IKLQLQAEER$|^{60}$GVVSIKGVDA$|^{70}$NRYLAMKE D$|^{80}$GRLLASKCVT$|^{90}$DECFFFERLE$|^{100}$SNNYNTYRST$|^{110}$KYTSWYVA LK$|^{120}$RTGQYKLGSK$|^{130}$TGPGQKAILFL$|^{140}$PMSAKS-COOH

SEQ ID NO. 2
NH2-NSDSECPLSHDGYCLHDGVCMYIEALDKYACNCVVGYIGERCQY RDLKWWELR-COOH

The invention claimed is:

1. A method of production of authentic human epidermal growth factor (EGF) and hyper-production of authentic basic fibroblast growth factor (bFGF) without any modification at either C- or N-terminal of the bFGF, comprising:

providing an Escherichia coli host;
introducing a DNA construct into the Escherichia coli host to produce a transformed Escherichia coli host, the DNA construct including an insert consisting of, in the order of, an expression cassette, a DNA coding for the EGF polypeptide, a first intein sequence, a first copy of a DNA coding for authentic bFGF, a second intein sequence, and a second copy of a DNA coding for the authentic bFGF, but being devoid of an ompA leader sequence;
subjecting the transformed Escherichia coli host to a fed-batch fermentation process;
wherein:
the DNA construct is configured to enable the transformed Escherichia coli host to produce the authentic bFGF in a soluble form cleaved and independent from proteins encoded by DNA regions preceding and subsequent to the authentic bFGF DNA codings in the insert, and intracellularly;
the fed-batch fermentation process is free of an induction step making use Isopropyl β-D-1-thiogalactopyranoside (IPTG);
the fed-batch fermentation process includes, during an early log-growth phase, a feeding step for a duration of time of 6 hours or less;
the fed-batch fermentation process includes, after the feeding step, a cultivation step for a duration of time of 7 hours or less; and
the Escherichia coli host is configured to produce the bFGF at a concentration at least two times more than a Escherichia coli host transformed with the DNA construct but without the second intein sequence and the second copy of a DNA coding for the authentic bFGF can.

2. A method as claimed in claim 1, wherein the concentration of the produced bFGF at the end of the cultivation step is 610 mg per liter of cell culture.

3. A method as claimed in claim 1, wherein the intein sequences are Saccharomyces cerevisiae vascular membrane ATPase (VMA).

4. A biological system engineered from an Escherichia coli host, comprising a DNA construct including an insert consisting of, in the order of, an expression cassette, a DNA coding for the EGF polypeptide, a first intein sequence, a first copy of a DNA coding for authentic bFGF, a second intein sequence, and a second copy of a DNA coding for the authentic bFGF, but being devoid of an ompA leader sequence;
wherein:
the DNA construct is configured to enable the transformed Escherichia coli host to produce the authentic bFGF in a soluble form cleaved and independent from proteins encoded by DNA regions preceding and subsequent to the authentic bFGF DNA codings in the insert, and intracellularly;
the system is configured to multiply in a fed-batch fermentation process; and
the Escherichia coli host is configured to produce the bFGF at a concentration at least two times more than a Escherichia coli host transformed with the DNA construct but without the second intein sequence and the second copy of a DNA coding for the authentic bFGF.

* * * * *

UNITED STATES PATENT AND TRADEMARK OFFICE
CERTIFICATE OF CORRECTION

PATENT NO. : 10,273,520 B2  
APPLICATION NO. : 15/409137  
DATED : April 30, 2019  
INVENTOR(S) : Kwong et al.

Page 1 of 1

It is certified that error appears in the above-identified patent and that said Letters Patent is hereby corrected as shown below:

On the Title Page

In the Application Priority Data item (60):  
Delete "Provisional application No. 61/808,602"  
Insert -- Provisional application No. 61/808,062 --

Signed and Sealed this  
Twentieth Day of August, 2019

Andrei Iancu  
*Director of the United States Patent and Trademark Office*